United States Patent [19]

Feliu et al.

[11] Patent Number: 5,259,944

[45] Date of Patent: Nov. 9, 1993

[54] CORROSION DETECTING PROBES FOR USE WITH A CORROSION-RATE METER FOR ELECTROCHEMICALLY DETERMINING THE CORROSION RATE OF REINFORCED CONCRETE STRUCTURES

[75] Inventors: Sebastian Feliu; Jose A. Gonzalez; Vicente Feliu; Sebastian Feliu, Jr.; M. Lorenza Escudero; Isabel A. Rodriguez-Maribona; Vicente Ausin; M. Carmen Andrade; Jose A. Bolano; Francisco Jimenez, all of Madrid, Spain

[73] Assignees: Geotecnia Y Cimientos, S.A.-Geocisa; Consejo Superior De Investigaciones Cientificas (CSIC), Madrid, Spain

[21] Appl. No.: 22,870

[22] Filed: Mar. 1, 1993

Related U.S. Application Data

[63] Continuation of Ser. No. 699,393, May 14, 1991, abandoned.

[30] Foreign Application Priority Data

May 18, 1990 [ES] Spain .................................. 9001392

[51] Int. Cl.⁵ ..................... G01N 27/26; G01N 27/416
[52] U.S. Cl. ............................... 204/404; 204/153.11
[58] Field of Search ..................... 204/153.11, 404; 324/425, 448, 71.2, 700

[56] References Cited

U.S. PATENT DOCUMENTS 4,861,453 8/1989 Matsuoka et al. ................. 204/404
4,958,130 9/1990 Mochizuki et al. ................ 324/700

OTHER PUBLICATIONS

S. Feliu et al., "Influence of Counter Electrode Size on the On-Site Measurement of Polarization Resistance in Concrete Structures", Paper No. 132, Corrosion 90, Apr. 23-27, 1990, Las Vegas, Nevada, pp. 142/1-142/6.
A. Sehgal et al., "Reproducibility of Polarization Resistance Measurements in Steel-in-Concrete Systems", Corrosion, Sep., 1992, vol. 48, No. 9, pp. 706-714.
A. Sehgal et al., "Comparison of Corrosion Rate-Measuring Devices for Determining Corrosion Rate of Settel-In-Concrete Systems", Corrosion, vol. 48, No. 10, pp. 871-880, Oct., 1992.
"Focus", Newsletter of the Strategic Highway Research Program, Washington, D.C., Sep. 1991, pp. 1-8.
Strategic Highway Research Program, Quarterly Progress Report on Contract No. SHRP-87-C101, "Assessment of Physical Condition of Concrete Bridge Components", Calender Quarter Ending Mar. 31, 1991, No. 11 of 15, by The Pennsylvania Transportation Institute, dated Apr. 12, 1991, pp. 1 and 15-34.

(List continued on next page.)

Primary Examiner—Aaron Weisstuch
Attorney, Agent, or Firm—Cushman, Darby & Cushman

[57] ABSTRACT

A corrosion detecting probe is to be used in combination with an electrochemical corrosion-rate meter for performing on-site diagnosis of the corrosion rate of metallic reinforcement systems in concrete structures. After the probe is brought into surface contact with a concrete member, voltage/current signals are applied thereto and a series of calculations are performed to determine the polarization resistance directly about a confined concrete portion. The probe consists essentially of an external counterelectrode, a central counterelectrode, a central reference electrode and a pair of extra reference electrodes (sensors). A current applied from the external counterelectrode serves to repel the lines of current (resulting from a voltage signal first applied at the central counterelectrode) below the probe and within the confined concrete portion which is between the central counterelectrode and the external one. The pair of sensors located on the surface of the concrete make it possible to fix the operating conditions so as to confine the measured area for which a polarization resistance is to be calculated. The sensors are necessary as they provide a substantially accurate indication of when the measured area is sufficiently confined as a function of the electrical signal field effects resulting from the voltage signal applied at the central counterelectrode and the current applied to the external counterelectrode.

2 Claims, 3 Drawing Sheets

OTHER PUBLICATIONS

S. Feliu et al., "Confinement of the Electrical Signal for In Situ Measurement of Polarization Resistance in Reinforced Concrete", ACI Materials Journal/Sep.-Oct. 1990, pp. 457-460.

J. A. Gonzalez et al., "On-Site Detection of Corrosion in Reinforced Concrete Structures", Materials and Structures, Rilem, 1991, 24, pp. 346-350.

S. Feliu et al., "Determining Polarization Resistance in Reinforced Concrete Slabs", Corrosion Science, vol. 29, No. 1, pp. 105-113 (1989).

V. Ausin et al., "Measurement of Corrosion Rate on R.C. Structures: A Contribution to the Assessment of Damaged Structures", Bulletin of the International Association for Shell Structures, No. 106, Sep. 1990, pp. 87-94.

L. M. Callow et al., "Corrosion Monitoring Using Polarization Resistance Measurements", British Corrosion J., vol. 11, No. 3, pp. 123-139 (1976).

J. E. Slater, "Corrosion of Metals in Association with Concrete", ASTM STP 818, Chapter V., pp. 35-43.

J. A. Gonzalez et al., "Errors in the Eelctrochemical Evaluation of Very Small Corrosion Rates", Corrosion Science, vol. 25, No. 10, pp. 917-930 (1985).

J. A. Gonzalez et al., "Errors in the Electrochemical Evaluation of Very Small Corrosion Rates", Corrosion Science, vol. 25, No. 7, pp. 519-530 (1985).

K. C. Clear, "Measuring Rate of Corrosion of Steel in Field Concrete Structures", Paper put out by Kenneth C. Clear, Inc., Sterling, Va., Jan. 1989, pp. 1-18.

S. Feliu et al., "Possibilities of the Guard Ring for the Confinement of the Electrical Signal of Polarization Measurements of Reinforcement", Corrosion 89, New Orleans, La, Apr. 1989 pp. 623/1-9.

S. G. McKenzie, *Corrosion Prevention& Control*, Feb. 1987, pp. 11-17.

CORROSION DETECTING PROBES FOR USE WITH A CORROSION-RATE METER FOR ELECTROCHEMICALLY DETERMINING THE CORROSION RATE OF REINFORCED CONCRETE STRUCTURES

This is a continuation of application Ser. No. 07/699,393, filed on May 14, 1991, which was abandoned.

BACKGROUND OF THE INVENTION

1. Field of the Invention

The present invention is directed to a device for electrochemically measuring the corrosion rate of a reinforced steel bar used in concrete structures, by non-destructive methods, with which a high measuring accuracy is obtained.

It is also an object of the invention to provide corrosion detecting probes for use with the device of the present invention.

2. Description of the Prior Art

Concrete is the most frequently used building material for all kinds of structures, such as houses, bridges, roads, dams, irrigation ditches, etc. The steel reinforcements embedded in these concrete structures remain indefinitely free of corrosion unless the concrete contains chlorides or it reacts with atmosphere carbon dioxide.

When the metal reinforcement corrodes, the rust build up breaks the concrete cover and this loss of physical integrity jeopardizes the structural integrity and load bearing capacity of the concrete structure.

Thus, diagnosis in situ of the metal structure corrosion rate is of high economic interest.

Leaving aside destructive methods, that is, those in which measurements are performed by partially destroying the structure, which cannot in a large majority of cases even be practiced, non-destructive methods are known, based on applying a small amplitude electrical signal to the reinforced steel bar and measuring the response it provokes.

The ratio between the applied potential and the response intensity is inversely proportional to the corrosion rate, and it is known as Polarization Resistance.

Its theoretical basis was given by Stern and other authors starting from 1957. For the value to be quantitative it is necessary that one know the area of a rebar (reinforced steel bar) to which the applied potential is being applied; thus can be calculated ampere/unit area values in the manner summarized in the article by S. G. McKenzie entitled, *Techniques for Monitoring Corrosion of Steel in Concrete*, Corrosion Prevention & Control, February, 1987, pg 1. In that article, the author emphasizes the importance of knowing the "area really affected by the applied signal". However, the author states that the direct use of the Apparent Polarization Resistance values does not reliably permit one to measure an on-site corrosion rate. McKenzie does not explain how to resolve this problem but only stresses the need to resolve it.

While conventional non-destructive methods as described in the McKenzie article offer acceptable results at the laboratory level where the extent of the metal area is known, such methods lack reliability in practice when applied to large structures, since for achieving this, it is mandatory to delimit or calculate the rebar area to which a measuring signal is applied.

As stated above, when dealing with real scale structures this problem poses a great obstacle in performing successful measurements. When applying an electrical signal, the signal will spread along the rebar until it reaches a critical length which is a function of the corrosion rate itself, of the concrete's water content (i.e., its resistivity), of the metal reinforcement surface, and of concrete thickness.

In order to overcome the above difficulty, different solutions have been tried and patented including U.S. Pat. No. 4,958,130 (18 Sep. 1990) and U.S. Pat. No. 4,861,453 (29 Aug. 1989), which disclose various devices, detecting probes and electrode arrangements for calculating True Polarization Resistance.

U.S. Pat. No. 4,958,130 discloses a method based essentially on measuring simultaneously three parameters: corrosion potential, polarization resistance and concrete ohmic resistance. These measurements are taken over in a plurality of points, and are functionally related to the concrete surface, the diameter of a reinforced steel bar, a sensor diameter and the gap between adjacent reinforced steel bars. The inventors claim they are able to obtain accurate values of True Polarization Resistance, however, no claim is made as to any specific corrosion detecting probes.

U.S. Pat. No. 4,861,453 discloses a corrosion detecting probe having a central counter and reference electrodes and another annular counter electrode, assembled in a material filled with a particular electrolyte which is electrically connected to a measuring device.

None of these references resolve accurately the calculation of a rebar area actually affected by an applied potential signal because:

a) the use of alternating current, even in the case where a guard ring is used, does not provide accurate values of the Polarization Resistance or does not allow an efficient confinement;

b) the calculations or methodology used are not well explained, nor do the references clarify or overcome the difficulty of making reliable measurements of the applied potential as it extends along a reinforcing bar.

SUMMARY OF THE INVENTION

The present invention is different from the prior art because it is based on a measuring device which uses D.C. signals and corrosion detecting probes with very specific electrode dispositions in order to obtain a True Polarization Resistance via CPU implemented computations which reliably account for rebar area difficulties encountered by an applied potential.

As an object of the present invention, True Polarization Resistance can be obtained as a function of the quotient obtained by dividing an applied potential with a measured response with reference to a rebar area and by monitoring the electrical field between a central counterelectrode and a guard ring electrode disposed therein, thus maintaining a controlled confinement.

More specifically, a central counterelectrode is again used having a corresponding reference electrode. Assembled again therewith is a surrounding (ring) electrode around the central counterelectrode which has a considerably larger diameter, and two reference (sensor) electrodes provided between the latter and the former in order to monitor that the surrounding electrode efficiently confines the electrical signal generated by the central counterelectrode.

In any case, the counterelectrode in a corrosion detecting probe is a metallic or other such electrical conductor material; and may be circular or may have some other geometric configuration (e.g., polygonal). The counterelectrode may also consist of a one piece structure or of fragmented portions in order to better form an electrical connection with the concrete surface.

In addition, corrosion detecting probes may be provided with a contact bed made of a spongy and flexible material offering the maximum adaptability to an irregular concrete surface. By keeping the contact bed continuously wet, a possible ohmic drop between a corrosion detecting probe, a reference electrode and the concrete can be minimized. On this note, corrosion detecting probes should also be provided with some appropriate system for maintaining a continuously wet environment.

The invention is also provided with the, necessary potentiostat/galvanostat circuits coupled to a data processing system for providing any necessary recording and processing/calculation of data.

BRIEF DESCRIPTION OF THE DRAWINGS

To complement the above description and in order to contribute to a better understanding of the invention, this specification includes a set of drawings in which, with an illustrative, non-limitative character, the following has been represented.

DETAILED DESCRIPTION OF THE PRESENTLY PREFERRED EXEMPLARY EMBODIMENTS

Figure 1:
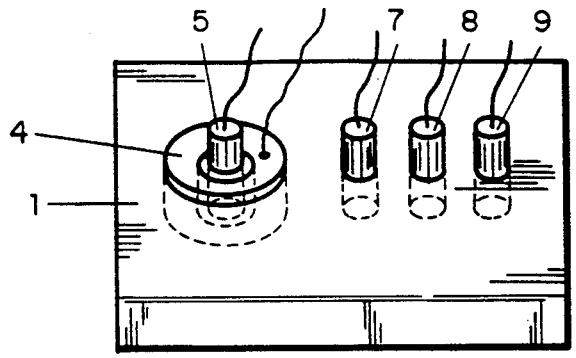
FIG. 1 shows a perspective schematic view of a corrosion detecting probe for performing potential attenuation along a known path to measure a corrosion rate of a large reinforced concrete structure according to a first embodiment of the present invention.

From these FIGURES and more specifically FIGS. 1 through 6 in each probe (1) a contact bed (2) is incorporated based on a spongy and flexible material having the ability to adapt itself to the irregular concrete surface (3), such contact bed should remain continuously wet in order to minimize the ohmic drop between the corrosion detecting probe and the concrete.

Each probe (1) incorporates one or more counterelectrodes which may be made of metal or any other electric conductor material, as well as one or more reference electrodes. Each probe (1) includes a central counterelectrode (4) having a central hole inside which a reference electrode (5) is housed, and which is connected to a corrosion-rate-meter (6) for measuring, recording and processing the data therefrom.

A corrosion detecting probe may be structured in the following different ways:

I. Probe for a measurement based on the apparent polarization resistance. The probe according to FIGS. 1 and 2, incorporates besides the central counterelectrode (4) and reference electrode (5), other reference electrodes (7),(8), and (9) which are disposed in a line with the central reference electrode.

II. A Probe for a measurement based on the polarization resistance value obtained which is a function of the counterelectrode area selected.

Figure 3:
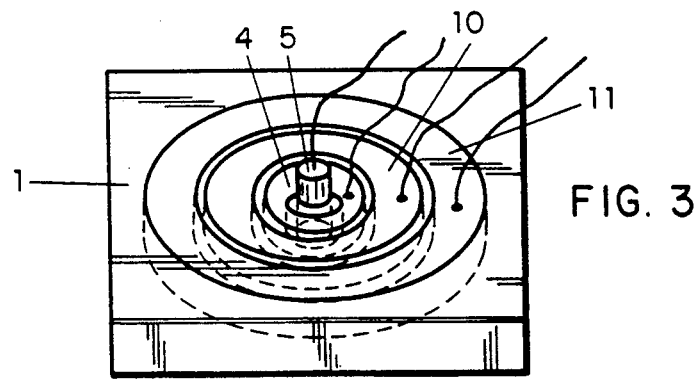
FIGS. 3 and 4 show a second embodiment of the present invention wherein a centrally disposed counterelectrode is surrounded by larger diameter ring counter electrodes for calculating corrosion rate.
Figure 4:
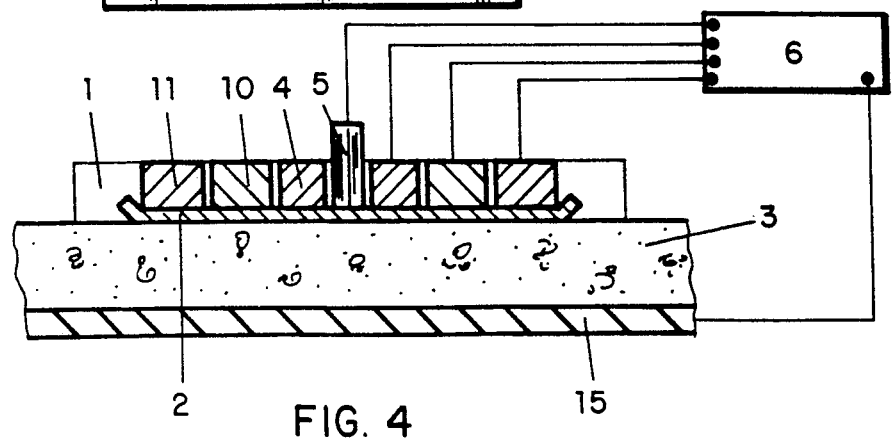

The probe shown in FIGS. 3 and 4 includes additional counterelectrodes 10 and 11, which are preferably ring shaped and concentric to central counterelectrode 4.

Figure 7:
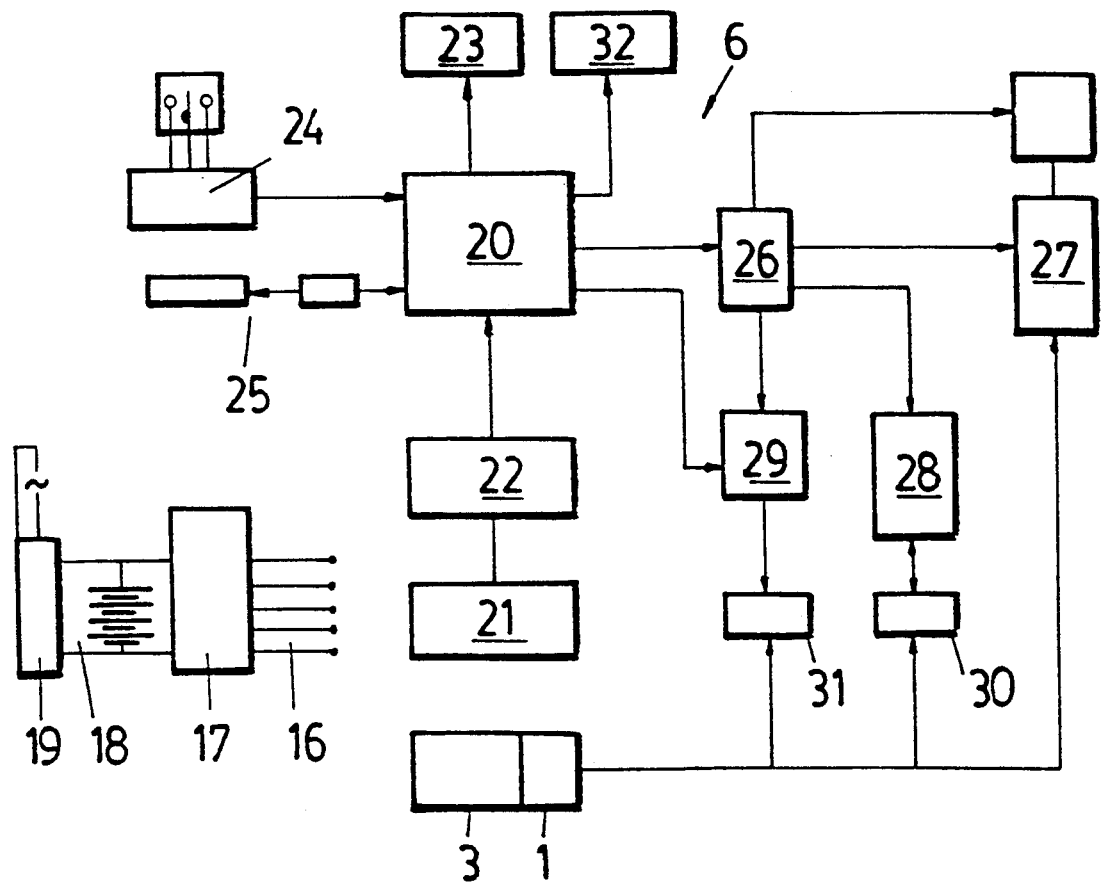
FIG. 7 shows a block diagram of a corrosion rate meter for use with the corrosion detecting probes shown in the above figures in accordance with the present invention.

These electrodes are electrically isolated and coupled only to the extent they are all connected by means of their respective connections to corrosion-rate-meter 6 shown by FIG. 7.

Figure 2:
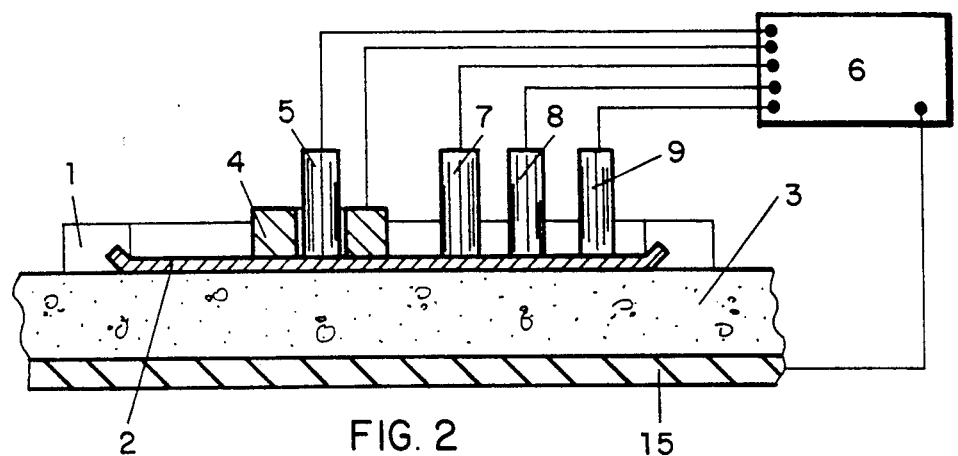
FIG. 2 shows a side elevation schematic view of the same corrosion detecting probe shown in FIG. 1, in working position and placed on the structure to be measured and connected to an external measuring device.

As in the embodiment of FIGS. 1 and 2, the dimensions of the counterelectrodes are not crucial to the proper operation of the invention.

III. Probe for measurement of the true polarization resistance obtained by means of efficiently confining an applied potential.

Figure 5:
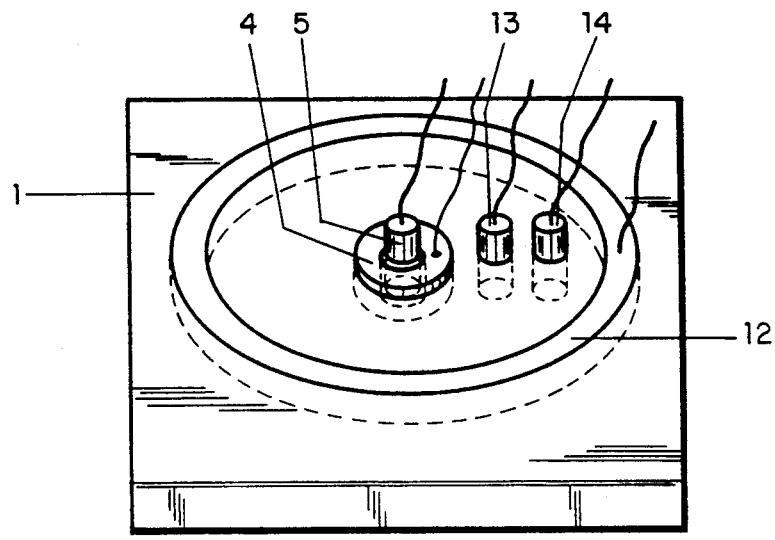
FIGS. 5 and 6 show a third embodiment of the present invention wherein a centrally disposed counterelectrode is surrounded by a guard ring electrode in a manner which selectively confines the measured area.
Figure 6:
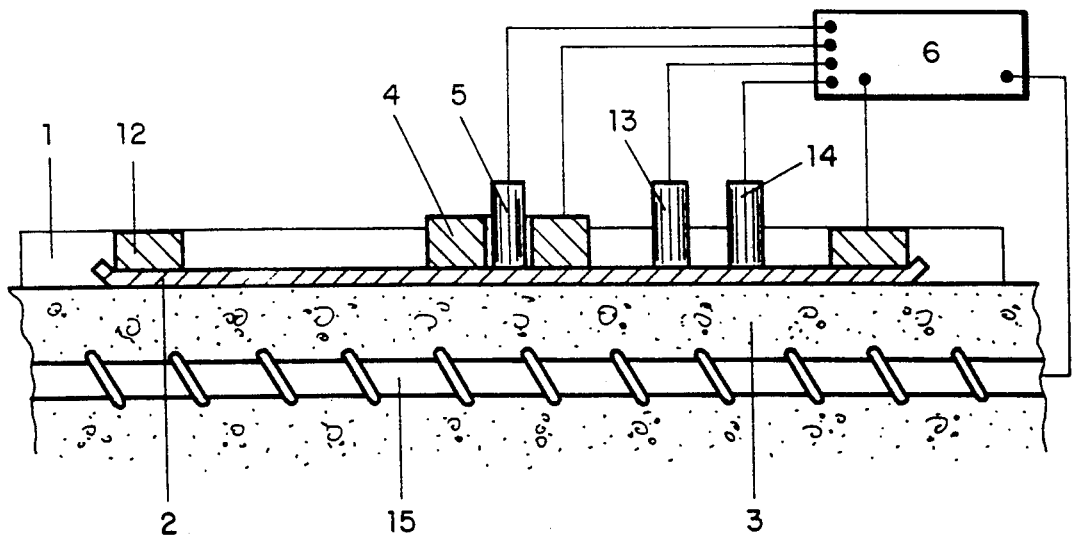

As may be seen from FIGS. 5 and 6, ring shaped electrode 12 concentric to central counterelectrode 4, receives from corrosion-rate-meter 6 a signal which can confine the signal produced by electrode 4 within an area perfectly delineated by a circle having a center inscribed by electrode 5 and passes through the central point between the reference (sensor) electrodes 1 3 and 14, aligned with the central reference electrode 5.

The dimensions of guard the ring electrode 12 and the position of the reference electrodes 13 and 14 are not critical.

In performing a measurement of the polarization resistance using a probe shown in FIGS. 1 and 2 the probe is first conveniently placed on the surface of concrete 3.

Subsequently, the various electrodes of the probe are electrically connected to corrosion-rate meter 6 shown in FIG. 7.

A reinforced steel bar 15 is also connected, through a perforation in the concrete, to corrosion rate meter 6.

Following this connection, the critical value corresponding to the reinforcement corrosion potential, as read with reference electrodes 5, 7, 8 and 9 are recorded in corrosion-rate meter 6.

Next, a potential (or current) is applied from corrosion-rate meter 6 to central counterelectrode 4 by means of a wire connector. This signal should not displace a corrosion potential reading by more than 20–25 mV. The response is recorded by corrosion-rate meter 6.

This measurement will be used in the calculation of the apparent polarization resistance. Immediately after a further signal is applied, large enough to produce significant variations on electrodes 7, 8, and 9, difference readings between prior and subsequent signal applications are recorded by corrosion-rate meter 6. These measurements will be used to determine the rebar area affected by the applied signals.

Corrosion-rate meter 6 calculates the true polarization resistance by way of software implemented routines which convert readings received from the probe into user readable data. These routines are strictly mathematical data crunching steps for solving well known interpretive relationships of known variables to calculate the true polarization resistance and effective corrosion rate.

In the embodiment of FIGS. 3 and 4 wherein increasing size electrodes are used, it becomes necessary to apply a number of electrical signals equal to the number of increasing area electrodes 10 and 11 being used at any one time. Similarly, an equal number of responses must be obtained. The response data is extrapolated and is a function of the electrode size and the type of concrete structure. Here again, the calculations necessary for extrapolation are carried out by corrosion-rate meter 6 using well known mathematical relationships.

In the embodiment of FIGS. 5 and 6 which confine an applied signal, the measurements by corrosion-rate meter 6 are based on the initial values corresponding to the corrosion potential of a rebar and the potential differences measured across reference electrodes 13 and 14.

A current (or voltage potential) is then applied between central counterelectrode 4 and rebar 15 which does not displace the reading of the corrosion potential measured by electrode 5 by more than 20-30 mV.

Immediately afterwards, another (current or voltage potential) signal is applied between external/confining counterelectrode 12 and rebar 15 until the potential across reference electrodes 13 and 14 returns to a value equal to that prior to the application of the first electrical signal from central counterelectrode 4. As soon as the response is stabilized, the current flowing through electrode 4 and rebar 15, as well as the average potential difference relative to electrode 5 are recorded by corrosion-rate meter 6.

With these values, a confined circular area of reinforcing bars can be delineated. Here again, corrosion-rate meter 6 can determine based on the electrode outputs a polarization resistance value and the corrosion rate of a rebar within a confined area.

FIG. 7 is a block diagram of corrosion-rate-meter 6 for use with the probes shown in any one of FIGS. 1 to 6. Corrosion-rate meter 6 includes a conventional continuous voltage converter 17, providing voltage outputs 16 of convenient polarity, thanks to a battery set 18 which is rechargeable by means of an external supply 19.

Corrosion-rate meter 6 further includes a CPU 20 coupled to ROM 21 and RAM 22 which store the software routines for performing any necessary calculations.

The corrosion-rate meter can be easily adapted to select among the three modes of operation discussed above in connection with the embodiments of FIGS. 1-2, 3-4, and 5-6, respectively.

The data processed by CPU 20 are made visual by alphanumeric display 23 made of LCD technology which is provided with the corresponding interface logic to CPU 20.

A keyboard 24 allows operator control including mode selection and data entry.

A bi-directional interface 25 permits transmission of data to/from—up to a maximum of 2400 baud—an auxiliary computer which may perform additional analysis and processing operations.

CPU 20 also controls D/A converters 26 which, in turn, give rise to the controlled voltage/current sources 27, 28 and to potentiostatic circuits 29, which are coupled via connector 30 and 31 to a sensor.

A power supply system 32 may be used to control battery charge or other kind of complementary information.

The operation of corrosion-rate meter 6 is as follows:
a) Performs initial measurements of reference potentials.
b) Provides selection of the measurement technique(s) most adequate as a function of the reference potential values measured in step (a) and as a function of additional operator input parameters.
c) Processes the data input from the corrosion detecting probe in accordance with a corresponding mode of selection determined in step (b).
d) Analyzes the measurements and calculates a corrosion rate of the measured concrete structure.

We claim:

1. An on-site corrosion rate meter for determining the corrosion rate by calculating polarization resistance of a metallic reinforcement disposed at least within a confined area of a concrete structure, the apparatus comprising:

corrosion detecting probe means comprising a plurality of electrodes adapted to be positioned on the surface of the concrete structure, and including:
an external counterelectrode concentrically positioned around a central counter electrode, said central counter electrode and external counterelectrode being electrically isolated from each other along said surface; and
a pair of adjacently disposed sensor electrodes positioned between said central counter electrode and said external counterelectrode and aligned with a central reference electrode, said central reference electrode being disposed within and insulated from said central counter electrode; and corrosion rate measuring means, coupled to said electrodes and the metallic reinforcement, to selectively apply signals thereto so as to confine the electrical field of action emanating from the central counterelectrode, said corrosion rate measuring means comprising:
recording means for recording an increase ($\Delta E$) in the reinforcement corrosion potential across the reference electrode and the metallic reinforcement, as well as an initial value of a relative potential difference across the pair of sensor electrodes;
bias means for applying an increasing first D.C. current source signal ($\Delta I$) across the central counter electrode and the metallic reinforcement to generate a first expanding electrical field of action at least within the confined area as delineated by the pair of sensor electrodes, said first expanding electrical field of action causing the relative potential difference across the pair of sensor electrodes to vary from the initial value;
counter electric field means for applying a second current source signal across the external counterelectrode and the metallic reinforcement to generate a second counter electrical field of action which serves to repel and confine the first expanding electrical field within the confined area delineated by the pair of sensor electrodes,
whereby the second current source signal is adapted to be applied with a maximum intensity necessary to return the relative potential difference across the pair of sensor electrodes to the initial value, at which time the recording means is adapted to record a final value of ΔE caused by a recorded final value of first D.C. current source signal (ΔI); and polarization resistance calculating means for calculating polarization resistance of the reinforced metallic member as a function of the size of the confined area as delineated by the pair of sensor electrodes, the recorded final value of ΔE, and the recorded final value of first D.C. current source signal (ΔT).

2. The apparatus of claim 1, wherein the electrodes are electrically isolated from each other and including a wet spongy material for providing electrolytic conduction among all the electrodes and the reinforced metallic member.

* * * * *